United States Patent [19]

Pepper

[11] Patent Number: 4,994,497
[45] Date of Patent: Feb. 19, 1991

[54] METHOD OF AVOIDING OR MINIMIZING BURN DAMAGE TO THE SKIN

[76] Inventor: Orlyn G. Pepper, 355 Everett, Milan, Mich. 48160

[21] Appl. No.: 419,698

[22] Filed: Oct. 11, 1989

[51] Int. Cl.$^5$ .......................... A61K 7/48; A61K 7/50
[52] U.S. Cl. .......................... 514/887; 424/DIG. 13; 424/195.1
[58] Field of Search ............... 424/DIG. 13; 514/886, 514/887, 828

[56] References Cited

U.S. PATENT DOCUMENTS

| | | | |
|---|---|---|---|
| 75,776 | 3/1968 | Lowdermill | 424/DIG. 13 |
| 4,784,842 | 11/1988 | London et al. | 424/195.1 |

FOREIGN PATENT DOCUMENTS 1261881  1/1972  United Kingdom ....... 424/DIG. 13

OTHER PUBLICATIONS

The Dispensatory of the United States of America, 25th Edition, title page, pp. 631–633.

*Primary Examiner*—Dale R. Ore
*Attorney, Agent, or Firm*—Krass & Young

[57] ABSTRACT

A method is provided of avoiding or minimizing inflammation at a painful freshly burned epidermal skin site, which comprises applying on the skin site promptly before the appearance of overt inflammation, an anti-inflammatory composition in homogeneous non-alcoholic aqueous solution form consisting essentially of distilled hamamelis water, magnesium sulfate, and copper sulfate to allow for transdermal absorption of the composition at the skin site for a period sufficient to achieve local relief of inflammatory symptoms.

9 Claims, No Drawings

METHOD OF AVOIDING OR MINIMIZING BURN DAMAGE TO THE SKIN

This invention relates to a first aid procedure and more particularly to a new and useful method of avoiding or minimizing acute burn damage to the skin.

BACKGROUND ART AND TERMINOLOGY

The American Illustrated Medical Dictionary by Dorland classifies burns of the skin as follows: "Burns of the first degree show redness, of the second degree, vesication, of the third degree, necrosis through the entire skin, and fourth degree, more or less charring."

In the typical metalwork or welding shop situation, the shop worker may from time to time be exposed unknowingly by direct contact of his person (e.g., the gloved or ungloved hand) with an extremely hot metal workpiece or a torch or the like. In such a case, the worker is burned, and he feels the burn pain immediately. However, and especially without first aid, he can only guess at the impending acute tissue damage to the burn site. If the burn site is left untreated, the pain may abate and the damage may amount to no more than temporary redness of the skin. However, if severe enough, the exposure may within hours result not only in redness and chronic pain, but sequelae such as vesication or blistering with exudation, and even breakage of the skin. It is common knowledge that, as a temporary measure, the discomfort and inflammation of such a burn can be alleviated by exposing the burn site to cold running water or an ice pack or cold compress.

The current treatment of choice for such burns is the application of an antiburn dermatological composition, usually in aerosol, liquid or ointment form which may include a "caine" type topical anesthetic or a topical antiseptic or germicide such as povidone-iodine. Some antiburn preparations also contain an alcohol, partly for its solvent action for organic solute components in the composition (see, for example, the patent to Lowdermill, U.S. Pat. No. 75,776). However, alcohol should not be applied to broken skin since irritation and burning can result.

It is therefore an object of the present invention to provide a method of avoiding or minimizing burn damage to the skin.

It is also an object to provide a method of treating burns in the work place which method will give immediate and at least temporary relief from pain and may avoid the serious tissue damage such as necrosis, vesication, breakage of the skin, or infection that might ensue if the burn site were left untreated.

These and other objects and advantages will be seen from the following description.

The invention in one preferred aspect concerns a method of avoiding or minimizing inflammatory sequelae to a painful freshly burned epidermal skin site. The method comprises in any suitable way applying to the surface of the skin site promptly before the appearance of overt inflammation, an anti-inflammatory composition, preferably to prevent contact of air with the skin site and preferably, to allow for transdermal absorption, as a covering layer or embrocation. The composition is in homogeneous non-alcoholic aqueous solution form, consisting essentially of distilled hamamelis water, magnesium sulfate, and cupric sulfate. If necessary from time to time, the composition or covering layer is replenished to allow for transdermal absorption of the composition at the site. Application is continued for a period sufficient to achieve local relief of inflammatory symptoms.

The composition can be applied in aerosol or liquid form, or in a preferred embodiment it can be applied by immersing or bathing the skin site in a quantity of the liquid composition. For the preparation of the composition, the hamamelis water, magnesium sulfate and cupric sulfate are mixed in suitable proportion which preferably is in parts by weight 73-92, 3-12, and 5-15, respectively. The hamamelis water preferably conforms in its preparation, e.g., to the aqueous phase (preferably 50% to full strength thereof) of the distillate "Hamamelis Water N.F." described in The Dispensatory of the United States of America, page 633, 25th Edition. It preferably contains a self-sterilizing agent such as methylparaben U.S.P. 0.1%. The magnesium sulfate preferably is the heptahydrate. The cupric sulfate preferably is the pentahydrate.

In one preferred embodiment the aqueous composition is made (e.g., at room temperature) by dissolving the magnesium sulfate in the hamamelis water and then dissolving the copper sulfate in the resulting solution, followed by mixing well and filtering the mixture to remove any solid particulates. When using the components in parts by weight as 1:8.3:1 (the hamamelis water weighing 8.3 pounds per gallon), the resulting composition contains in weight percent magnesium sulfate and copper sulfate 9.7% each and hamamelis water 80.6%.

For best results in treating the typical fresh skin burn such as one resulting from touching hot metal (or a similar skin burn), the composition as described is applied freely (suitably as a covering layer) to the affected area several times (e.g., four times) at short (e.g., 10-minute) intervals. Typically, the pain is relieved each time. Further application is made as needed to relieve any recurring pain. Surprisingly, such application not only relieves the pain, but also has a shrinking effect and reduces the swelling and inflammation that would otherwise result in the absence of treatment. Such treatment even avoids blistering in the typical case. The treatment typically may continue for one to two hours but thereafter is no longer required. This early relief enables the worker not only to avoid lost work time but also to forego further medical attention unless absolutely necessary.

The embodiments of my invention in which an exclusive property or privilege is claimed are defined as follows.

I claim:

1. A method of avoiding or minimizing inflammatory sequelae to a painful freshly burned epidermal skin site, which comprises applying to the surface of the skin site promptly before the appearance of overt inflammation, an anti-inflammatory composition in homogeneous non-alcoholic aqueous solution form consisting essentially of distilled hamamelis water, magnesium sulfate, and copper sulfate to allow for transdermal absorption of the composition at the site for a period sufficient to achieve local relief of inflammatory symptoms.

2. A method according to claim 1 where the composition includes in parts by weight percent hamamelis water (73-92), magnesium sulfate (3-12), and copper sulfate (5-15).

3. A method according to claim 2 where the hamamelis water contains a self-sterilizing agent.

4. A method according to claim 1 where the composition is applied to the burn site topically at short intervals until local relief of inflammatory symptoms is achieved.

5. A method according to claim 1 where the composition is applied to the skin site in a covering layer.

6. A method according to claim 1 where the composition is applied by immersing the skin site therein.

7. A method according to claim 2 where the composition includes the components in the ratio 80.6:9.7:9.7.

8. A method according to claim 1 where the magnesium sulfate is the heptahydrate.

9. A method according to claim 1 where the copper sulfate is the pentahydrate.

* * * * *